(12) United States Patent
Matricardi et al.

(10) Patent No.: US 10,059,811 B2
(45) Date of Patent: Aug. 28, 2018

(54) POLYMER PLATFORM TO PREPARE NANOHYDROGEL

(71) Applicants: Pietro Matricardi, Rome (IT); Chiara Di Meo, Bucchianico (IT)

(72) Inventors: Pietro Matricardi, Rome (IT); Chiara Di Meo, Bucchianico (IT); Claudio Villani, Rome (IT)

(73) Assignees: Pietro Matricardi, Rome (IT); Chiara Di Meo, Bucchianico (IT)

( * ) Notice: Subject to any disclaimer, the term of this patent is extended or adjusted under 35 U.S.C. 154(b) by 78 days.

(21) Appl. No.: 15/036,191

(22) PCT Filed: Nov. 14, 2014

(86) PCT No.: PCT/IB2014/066054
§ 371 (c)(1),
(2) Date: May 12, 2016

(87) PCT Pub. No.: WO2015/071873
PCT Pub. Date: May 21, 2015

(65) Prior Publication Data
US 2016/0289394 A1    Oct. 6, 2016

(30) Foreign Application Priority Data
Nov. 15, 2013    (IT) .............................. RM2013A0631

(51) Int. Cl.
| | | |
|---|---|---|
| *C08J 3/075* | (2006.01) | |
| *A61K 31/5383* | (2006.01) | |
| *A61K 31/337* | (2006.01) | |
| *A61K 9/51* | (2006.01) | |
| *A61K 9/06* | (2006.01) | |
| *A61K 47/36* | (2006.01) | |
| *A61K 9/107* | (2006.01) | |

(52) U.S. Cl.
CPC ................. *C08J 3/075* (2013.01); *A61K 9/06* (2013.01); *A61K 9/1075* (2013.01); *A61K 9/5161* (2013.01); *A61K 31/337* (2013.01); *A61K 31/5383* (2013.01); *A61K 47/36* (2013.01); *C08G 2210/00* (2013.01); *C08J 2305/00* (2013.01); *C08J 2305/08* (2013.01)

(58) Field of Classification Search
CPC ...... A61K 9/1075; A61K 9/5161; A61K 9/06; A61K 31/337; A61K 31/5383; A61K 47/36; C08G 2210/00; C08J 3/075; C08J 2305/00; C08J 2305/08
See application file for complete search history.

(56) References Cited

PUBLICATIONS

PCT, International Search Report and Written Opinion, International Application No. PCT/IB2014/066054, dated Apr. 29, 2015.
El Ghaffar, M.A. Abd et al., "pH-sensitive sodium alginate hydrogels for riboflavin controlled release," *Carbohydrate Polymers*, vol. 89, No. 2, pp. 667-675, Jun. 1, 2012.
D'Arrigo, Giorgia et al., "Self-assembled gellan-based nanohydrogels as a tool for prednisolone delivery," *Soft Matter*, vol. 8, No. 45, pp. 11557-11564, Jan. 1, 2012.
Montanari, Elita et al., "Hyaluronic Acid Nanohydrogels as a Useful Tool for BSAO Immobilization in the Treatment of Melanoma Cancer Cells," *Macromolecular Bioscience*, 13, 1185-1194, 2013.

*Primary Examiner* — Johann R Richter
*Assistant Examiner* — Genevieve S Alley
(74) *Attorney, Agent, or Firm* — FisherBroyles, LLP; Susan M. Oiler

(57) ABSTRACT

Methods to prepare nanohydrogels are disclosed that include functionalizing a polysaccharide with a hydrophobic compound to form a functionalized polysaccharide, and subjecting the functionalized polysaccharide to a self-assembling process in a water environment for the formation of the nanohydrogel. The hydrophobic compound is riboflavin, or a derivative thereof, to which an alkyl group having a functional group suited to form a covalent bond with the polysaccharide has been bonded.

9 Claims, No Drawings

POLYMER PLATFORM TO PREPARE NANOHYDROGEL

CROSS-REFERENCE TO RELATED APPLICATIONS

This application is a National Stage filing of International Application No. PCT/IB2014/066054, filed Nov. 14, 2014, which claims priority of Italian Patent Application No. RM2013A000631, filed Nov. 15, 2013, which are incorporated herein by reference in their entireties.

TECHNICAL FIELD

The present invention concerns the development of a new polymer platform to prepare nanohydrogel by self-assembling.

The term nanohydrogel indicates a particular type of nanoparticle with dimensions ranging from 10 to 1000 nm able to combine the advantages of hydrogels with those of nanotechnology, for example high flexibility, versatility, water absorption, high biocompatibility and long residence times inside the organism.

BACKGROUND ART

In general, it is known that a polysaccharide (with hydrophilic character) appropriately functionalized with molecules having hydrophobic character can produce an assembling system with nanohydrogel characteristics if exposed to particular conditions in a water environment.

Nanohydrogels are acquiring considerable importance in pharmaceutical terms since they can be used as carrier compounds for drugs and be administered both in humans and animals by inhalation, parenterally (i.v, i.m, s.c.) or topically supported by an appropriate device and/or dispersant means.

Currently, different methods are known for the preparation of functionalized polysaccharides for the preparation of nanohydrogel, the most famous of which is derivatization of the polymer chains with derivatives of cholesterol or colanic acid. Said molecules appropriately bonded to the polysaccharide chains give the system the right amphiphilicity such as to allow the process of self-assembling in water and/or physiological solutions, after appropriate treatment of the compound.

A first of these treatments consists in subjecting the functionalized polysaccharide to sonication. The ultrasonic vibrations are able to induce the formation of small-dimension nanohydrogel. The ultrasounds generate in the polymer suspension micro-bubbles which, by imploding, give rise to the phenomenon of cavitation which promotes separation of the polymer chains favouring the formation of a nanoparticle suspension. Another method consists in solubilising the functionalized polysaccharide in an appropriate solvent and adding dropwise the solution obtained in water. In these conditions the system precipitates inducing the formation of nanoparticles. Yet another method consists in subjecting the functionalized polysaccharide to dialysis against water or water solution once said polysaccharide has been solubilised in an organic solvent. The slow inlet of water through the dialysis tubes causes the formation of small-dimension nanohydrogel by spontaneous self-assembling.

As mentioned above, one of the possible applications of nanohydrogels is in pharmaceutical preparations administered parenterally. The nanohydrogel can incorporate a pharmacologically active ingredient and function as a carrier for the administration thereof.

In this context, the capacity of the polymer derivative to give rise to nanohydrogel with satisfactory yield, the stability of said nanohydrogels in both conservation conditions and in water and physiological fluids, and the yield of the bioactive molecule loading process, in addition to the possibility of being sterilised for systemic administration without causing drug loss are essential requirements.

Currently the nanohydrogel systems present in the literature are unsuitable for industrial use also due to the low yields obtained after purification and the low degree of drug loading that can be obtained. Due to the high water content of the nanohydrogel systems, in fact, separation and concentration by means of ultracentrifugation is often insufficient or in any case produces low yields. The nature of the hydrophobic domains within the nanohydrogel, furthermore, is often inadequate for a high loading of drugs.

The need was therefore felt for a more effective polymer platform in terms of formation of nanohydrogel, in terms of loading of drugs and in terms of stability of the nanohydrogels formed in both physiological conditions and in conservation conditions.

The inventors of the present patent application have found an extremely versatile method of synthesis of amphiphilic derivatives of polysaccharides for the preparation of nanohydrogels responding to the above needs.

DISCLOSURE OF INVENTION

The subject of the present invention is a method to prepare nanohydrogel comprising the steps of:
hydrophobic functionalization, in which a polysaccharide is functionalized with a hydrophobic compound;
self-assembling, in which the functionalized polysaccharide obtained from the preceding step is subject to a self-assembling process in a water environment for the formation of nanohydrogel;
said method being characterised in that said hydrophobic compound is riboflavin, or a derivative thereof, which is bound to an alkyl group having a functional group suited to form a covalent bond with the polysaccharide.

Preferably the riboflavin derivative is an ester or urethane derivative obtained through reaction on hydroxyl groups of the riboflavin.

Preferably, the riboflavin derivative is tetrabutylriboflavin or tetraacetylriboflavin.

Preferably, the alkyl group is a straight chain containing 2 to 20 atoms and said functional group is suited to react with the —OH or —NH groups available on the riboflavin, forming ester bonds, amide bonds, ether bonds or urethane bonds.

Preferably, the alkyl group is a straight chain containing 3 to 8 carbon atoms.

Preferably, the polysaccharide used can have the nature of a polyanion, a polycation or a neutral nature and a molecular weight ranging from 2,000 to 1,500,000 and form, with the riboflavin or with the riboflavin derivative, ester bonds, amide bonds, ether bonds or alkyl bonds with a derivatization percentage ranging from 2 to 100% mol/mol.

Preferably, the polysaccharide is comprised in the group consisting of hyaluronic acid, pullulan, dextran, gellan, scleroglucan, chitosan, alginate, guar, xanthan, chitosan, cyclodextrins.

A further subject of the present invention are nanohydrogel particles manufactured with the method subject of the present invention.

A further subject of the present invention are nanohydrogel particles manufactured with the method subject of the present invention and loaded with a pharmacologically active compound.

The pharmacologically active compound can be physically loaded in the nanogels or chemically bonded on their surface and/or within them.

The physically loaded pharmacologically active compound is added to the water dispersion of the polysaccharide derivative before the heating or sonication process, or is dissolved in the organic phase where the polysaccharide derivative is dissolved before the nanoprecipitation, or is dissolved in the water phase in which the nanoprecipitation occurs. A further method is represented by the formation of a drug film obtained by evaporation of solvent; said film is then placed in contact with a nanohydrogel suspension so as to induce loading of the active ingredient within the nanosystems.

Preferably, said pharmacologically active compound is added to the water dispersion of the polysaccharide in a concentration ranging from 0.05 mg/ml to 20.0 mg/ml.

Preferably, said pharmacologically active compound is dissolved in the organic phase in which the polysaccharide derivative is dissolved in a concentration ranging from 0.05 mg/ml to 20.0 mg/ml.

Preferably, said pharmacologically active compound is dissolved in the water phase in which the polysaccharide derivative is nanoprecipitated in a concentration ranging from 0.05 mg/ml to 20.0 mg/ml.

Preferably, for formation of the film, said pharmacologically active compound is dissolved in an appropriate volatile organic solvent in a concentration ranging from 0.05 mg/ml to 20.0 mg/ml.

The chemically bonded pharmacologically active compound is added to the nanogel suspension and made to react by means of appropriate reagents with the polymer derivative via the functional groups present. Preferably, the pharmacologically active compound is bonded by means of a spacer arm to the nanogel surface via ester or amide bond exploiting a chemical reaction, for example the chemistry of carbodiimides.

Preferably, said pharmacologically active compound is comprised in the group composed of antibiotics, antitumoral drugs, analgesics, anti-inflammatories, anaesthetics, analeptics, adrenergic agents, adrenergic blocking agents, anticholinergics, acetylcholinesterase inhibitors, anticonvulsants, adrenocorticotrophic, adrenolytics, adrenomimetics, alkylating agents, alkaloids, allosteric inhibitors, anabolic steroids, anorectics, antiacids, antidotes, anti-diarrhoeal drugs, antifolic, antipyretics, antirheumatics, psychotherapeutic agents, neural blocking agents, antiemetics, anthelmintics, antiarrhythmics, antitubercular drugs, anticoagulants, antidepressants, antidiabetics, antiepileptics, antifungals, antihistamines, antihypertensives, antimuscarinics, antimycobacterials, antimalarials, antiseptics, antiprotozoal drugs, immunosuppressors, immunostimulants, antithyroid drugs, antivirals, anxyolitics, sedatives, astringents, beta blockers, contrast media, corticosteroids, antitussives, diagnostic agents, diagnostic imaging agents, diuretics, dopaminergics, haemostatics, haematological agents, haemoglobin modifiers, hormones, hypnotics, hypolipidemizing agents, lipid regulating agents, muscarinics, parasympathomimetics, myorelaxants, prostaglandins, sedatives, sex hormones, antiallergens, stimulants, sympathomimetics, thyroid agents, vasodilators, vaccines, vitamins, xanthines, antineoplastics, proteins, polypeptides, carbohydrates, polynucleotides, nucleic acids, polyclonal or monoclonal antibodies.

BEST MODE FOR CARRYING OUT THE INVENTION

EXAMPLES

For a better understanding of the invention, embodiment examples are given below for illustrative non-limiting purposes.

In the following examples the dimensions of the nanohydrogel particles were measured with the Dynamic Light Scattering technique (Submicron Particle Sizer Autodilute Model 370, Nicomp).

In the present invention the self-assembling step can be performed:

by water dispersion of the product and a heating step in which the water dispersion of the polysaccharide is subject to a temperature ranging from 70 to 150° C. and to a pressure ranging from 1 to 5 bar. The temperature and pressure conditions must be such that boiling of the polysaccharide water dispersion does not occur;

by water dispersion of the product and exposure to ultrasounds by means of ultrasonic bath for a time varying between 2 min and 3 hours. In this case, the exposure to ultrasounds via ultrasonic bath preferably occurs for a time ranging from 5 to 90 min at a frequency of 20-40 kHz;

by solubilization of the product in an appropriate organic solvent and subsequent nanoprecipitation in water or water solvent, followed by dialysis to remove the organic phase.

Example 1

Formation of Hyaluronic-Riboflavin (HA-Rfv) Nanohydrogel From Derivatized Polymer at 30% mol/mol The hyaluronic acid was appropriately functionalized with hydrophobic units of tetrabutylriboflavin so as to obtain an amphiphilic polymer (hyaluronic-riboflavin, HA-Rfv) in the form of a macromolecular agglomerate.

500 mg of tetrabutylriboflavin were solubilized in 4.5 mL of anhydrous dimethylformamide (DMF); 158 mg of anhydrous potassium carbonate were added and the dispersion was left for 45 minutes under stirring in a nitrogen atmosphere. In parallel, a solution of 0.470 mL of 1.6-dibromohexane in 2.5 mL of DMF was prepared and this was added dropwise to the dispersion, which was then left under stirring for 5 hours. At the end, 20 mL of dichloromethane were added to the reaction mixture and the solution was extracted in a separator funnel 3 times with an equal volume of water; the organic phase was then separated and dehydrated on anhydrous sodium sulphate and evaporated to dryness by means of rotavapor. The product N-(6-bromohexyl)-tetrabutylriboflavin was purified by means of chromatographic column ($SiO_2$, dichloromethane:ethyl acetate 75:25).

100 mg of hyaluronic acid in the form of tetrabutylammonium (HA) salt were dissolved in 10 mL of N-methylpyrrolidone (NMP) at ambient temperature; 37.4 mg of N-(6-bromohexyl)-tetrabutylriboflavin were dissolved in 1 mL of NMP and the solution was added to that of the polymer, leaving under stirring for 48 hours at ambient temperature. The reaction was then dialysed (cut-off 12000-14000) and lyophilised, obtaining 120 mg of derivative as a yellow lyophile (HA-Rfv). The degree of derivatization of the polymer was equal to 30% mol/mol (moles of Rfv based on moles of repetitive units of HA, determined by spectrophotometer).

3 mg of the product were dispersed in 3 ml of water and the solution was left under stirring on a plate for 12 hours. The dispersion deriving from the water solution was placed inside a closed glass container which was placed in an autoclave. In the autoclave the dispersion was subject for 20 minutes to a temperature of 121° C. and a pressure of 2 bar. At the end of the treatment nanohydrogels of HA-Rfv with dimensions of 330±15 nm were obtained, with a polydispersion index of 0.15±0.05.

The dimensional stability of the nanohydrogels of HA-Rfv was studied at 37° C. for 15 days so as to mime the physiological conditions, and at 4° C. for 15 days so as to mime the conservation conditions of the product in the refrigerator. The nanohydrogels of HA-Rfv formed at high T and high P proved to be stable at high and low conservation temperature.

The dimensional stability of the nanohydrogels of HA-Rfv was also studied at ambient temperature in a water solution of NaCl 0.9% w/V, showing that the system is stable in these conditions for over one week.

Example 2

Formation of Pullulan-Riboflavin (Pul-Rfv) Nanohydrogel

The pullulan was appropriately functionalized with hydrophobic units of tetrabutylriboflavin so as to obtain an amphiphilic polymer (pullulan-riboflavin, Pul-Rfv) in the form of a macromolecular agglomerate.

100 mg of pullulan (Pul) were dissolved in 2 mL of anhydrous dimethyl sulfoxide (DMSO) at ambient temperature; 20 mg of dimethylaminopyridine (DMAP) were then added to the solution. 40 mg of N-(6-bromohexyl)-tetrabutylriboflavin prepared as described in example 1 were dissolved in 0.5 mL of NMP and the solution was added to the polymer solution, leaving under stirring for 48 hours at ambient temperature. The reaction was then dialysed (cut-off 12000-14000) and lyophilised, obtaining 110 mg of derivative as yellow lyophile (Pul-Rfv). The degree of derivatization of the polymer was 8% mol/mol (moles of Rfv based on moles of repetitive units of Pul).

5 mg of the amphiphilic polymer (Pul-Rfv) were dispersed in 3 ml of water and the solution obtained was left under stirring on a plate for 12 hours. The dispersion obtained was placed inside an appropriate closed glass container which was placed in an ultrasonic bath and subject to ultrasounds for 20 min.

At the end of the treatment, Pul-Rfv nanohydrogels were obtained having dimensions of 220±20 nm, with a polydispersion index of 0.20±0.05.

The stability of the Pul-Rfv nanohydrogels was studied at 4° C. for 7 days so as to mime the conservation conditions of the product in the refrigerator. The Pul-Rfv nanohydrogels formed by means of ultrasonication proved to be stable at low conservation temperature for over 7 days. The dimensional stability of the Pul-Rfv nanohydrogels was also studied at ambient temperature in a water solution of NaCl 0.9% w/V, showing that the system is stable in these conditions for longer than 72 hours.

Example 3

Formation of Hyaluronic-Riboflavin (HA-Rfv) Acid Nanohydrogel From Derivatized Polymer at 20% Mol/mol The hyaluronic acid was appropriately functionalized with hydrophobic units of tetracetylriboflavin so as to obtain an amphiphilic polymer (hyaluronic-riboflavin, HA-Rfv) in the form of a macromolecular agglomerate.

500 mg of tetraacetylriboflavin were solubilized in 4.5 mL of anhydrous dimethylformamide (DMF); 126 mg of anhydrous potassium carbonate were added and the dispersion was left for minutes under stirring in a nitrogen atmosphere. In parallel, a solution of 0.350 mL of 1.4-dibromobutane in 2.5 mL of DMF was prepared and this was added dropwise to the dispersion, which was then left under stirring for 5 hours. At the end, 20 mL of dichloromethane were added to the reaction mixture and the solution was extracted in a separator funnel 3 times with an equal volume of water; the organic phase was then separated and dehydrated on anhydrous sodium sulphate and evaporated to dryness by means of rotavapor. The product N-(4-bromobutyl)-tetraacetylriboflavin was purified by chromatographic column ($SiO_2$, dichloromethane:ethyl acetate 75:25).

50 mg of hyaluronic acid (HA) were dissolved in 5 mL of N-methylpyrrolidone NMP) at ambient temperature; 12.5 mg of N-(4-bromobutyl)-tetraacetylriboflavin were dissolved in 0.5 mL of NMP and the solution was added to the polymer solution, leaving under stirring for 48 hours at ambient temperature. The reaction was then dialysed (cut-off 12000-14000) and lyophilised, obtaining 65 mg of derivative as yellow lyophile (HA-Rfv). The degree of derivatization of the polymer was 20% mol/mol (moles of Rfv based on moles of repetitive units of HA).

3 mg of the product were dispersed in 3 ml of water and the resulting solution was left under stirring on a plate for 12 hours. The dispersion deriving from the water solution was placed inside a closed glass container, which was placed in an ultrasonic bath and subject to ultrasounds for 25 min.

At the end of the treatment, HA-Rfv nanohydrogels were obtained having dimensions of 250±20 nm, with a polydispersion index of 0.10±0.05. The ζ Potential of the nanohydrogels was −30±5.0 mV.

The dimensional stability of the HA-Rfv nanohydrogels was verified at 37° C. for 7 days and at 4° C. for 30 days, showing stability of the NH suspensions. The dimensional stability of the HA-Rfv nanohydrogels was also studied at 37° C. in RPMI cell culture medium with the addition of 10% fetal bovine serum, showing stability of the system for 48 hours.

Example 4

Formation of Gellan-Riboflavin (Ge-Rfv) Nanohydrogel

The gellan was appropriately functionalized with hydrophobic units of tetrabutylriboflavin so as to obtain an amphiphilic polymer (gellan-riboflavin, Ge-Rfv) in the form of a macromolecular agglomerate.

50 mg of gellan (Ge) in the form of tetrabutylammonium salt were dissolved in 15 mL of N-methylpyrrolidone (NMP) at ambient temperature; 11 mg of N-(4-bromobutyl)-tetraacetylriboflavin, prepared as described in example 3, were dissolved in 0.5 mL of NMP and the solution was added to the polymer solution, leaving under stirring for 48 hours at 38° C. The reaction was then dialysed (cut-off 12000-14000) and lyophilised, obtaining 60 mg of derivative as yellow lyophile (Ge-Rfv). The degree of derivatization of the polymer was 10% mol/mol (moles of Rfv based on moles of repetitive units of Ge).

1.5 mg of the amphiphilic polymer (Ge-Rfv) were dispersed in 3 ml of water and the resulting solution was left under stirring on a plate for 12 hours. The dispersion obtained was placed inside a closed glass container, which was placed in an autoclave. In the autoclave the dispersion was subject for 15 minutes to a temperature of 130° C. and a pressure of 2.5 bar. At the end of the treatment, Ge-Rfv nanohydrogels were obtained having dimensions of 350±20 nm, and with a polydispersion index of 0.25±0.10.

Example 5

Formation of Gellan-Riboflavin (Ge-Rfv) Nanohydrogel and Loading with the Antitumoral Drug Paclitaxel By Means of Film Casting Method The amphiphilic polymer Ge-Rfv in the form of a macromolecular agglomerate was dispersed in a water solution (0.5 mg/ml) and left under stirring on a plate at ambient temperature for 12 hours. The dispersion obtained was placed in a closed glass container which was placed in an autoclave. In the autoclave the dispersion was subject for 15 minutes to a temperature of 130° C. and a pressure of 2.5 bar. At the end of the treatment, Ge-Rfv nanohydrogels were obtained having dimensions of 350±20 nm, with a polydispersion index of 0.25±0.10.

In parallel, 250 mg of paclitaxel were solubilised in 0.5 mL of methanol in a flask and the solvent was evaporated by means of a rotavapor, forming a dry film of the drug. The Ge-Rfv NH dispersion was then added to the flask with the paclitaxel film and left for 20 hours under gentle magnetic stirring. Subsequently, the suspension was centrifuged (2000 rpm for 10 min) to precipitate the non-loaded paclitaxel; the entrapment effectiveness (encapsulation %) was determined by the difference between the quantity of paclitaxel not encapsulated in the nanohydrogels and resolubilised in methanol, and the total quantity of paclitaxel used, with respect to the total quantity of nanohydrogels produced by means of HPLC analysis. The entrapment effectiveness of the paclitaxel in the Ge-Rfv nanohydrogels was 9% with respect to the weight of the polymer.

Example 6

Formation of Hyaluronic-Riboflavin (HA-Rfv) Nanohydrogel and Loading with the Antibiotic Levofloxacin via Autoclave and Comparison with the HA-Cholesterol System The amphiphilic polymer HA-Rfv (derivatization degree 30% mol/mol) in the form of macromolecular agglomerate prepared as described in example 1 was dispersed in water solution (1 ml, 1 mg/ml) and left under stirring on a plate at ambient temperature for 12 hours. 1 ml of a solution of 0.66 mg/ml of a fluoroquinolone antibiotic (levofloxacin) was then added to the dispersion, thus obtaining a final antibiotic concentration of 0.33 mg/ml. The mixture thus obtained was placed in a suitable closed glass container arranged inside an autoclave. In the autoclave the dispersion was subject for 20 minutes to a temperature of 121° C. and a pressure of 2 bar.

At the end of the process, the dispersion was subject to dialysis (Visking tubing, cut-off: 12000-14000) for 3 hours against distilled water so as to purify the nanohydrogels of the non-encapsulated drug inside them.

After the dialysis, HA-Rfv nanohydrogels were obtained loaded with levofloxacin having dimensions of 330±30 nm, with a polydispersion index of 0.20±0.05.

For the preparation of HA-cholesterol (HA-CH) NHs starting from derivatized polymer at 20% mol/mol, the procedure reported in literature was followed (E. Montanari, S. Capece, C. Di Meo, M. Meringolo, T. Coviello, E. Agostinelli, P. Matricardi, Macromolecular Bioscience 2013; 13, 1185-1194). In short, 500 mg of cholesterol were solubilized in 5 mL of dichloromethane ($CH_2Cl_2$) and 79 mg of dimethylaminopyridine (DMAP) were then added. Separately, 648 mg of 4-bromobutyric acid together with 744 mg of N(3-Dimethylaminopropyl)-N'-ethylcarbodiimide hydrochloride (EDC.HCl) were solubilised in 5 mL of $CH_2Cl_2$. The solutions were mixed and the reaction was carried out for 12 hours at ambient temperature. The solution was then purified by extraction with NaOH 0.05M, HCl 0.05M and $H_2O$, the organic solvent was dried on anhydrous $NaSO_4$ and evaporated in a vacuum by means of rotavapor. The reaction product was then purified by means of chromatographic column ($SiO_2$, eluent cyclohexane:ethylacetate 99:1), obtaining approximately 500 mg of cholesterol-bromobutyrate (HA-Br).

200 mg of hyaluronic acid in the form of tetrabutylammonium salt (HA) were dissolved in 10 mL of N-methylpyrrolidone (NMP) at ambient temperature; 34.3 mg of CH-Br were dissolved in 2 mL of NMP and the solution was added to that of the polymer, leaving under stirring for 48 hours at 38° C. The reaction was then dialysed (cut-off 12000-14000) and lyophilised, obtaining 190 g of derivative as white lyophile (HA-CH). The degree of derivatization of the polymer was 20% mol/mol (moles of CH based on moles of repetitive units of HA, determined by means of 1H-NMR).

1 mg of the product was dispersed in 1 ml of water and left under stirring on a plate for 12 hours. 1 ml of a solution of 0.66 mg/ml of a fluoroquinolone antibiotic (levofloxacin) was then added to the dispersion, thus obtaining a final antibiotic concentration of 0.33 mg/ml. The mixture thus obtained was placed in a suitable closed glass container which was arranged inside an autoclave. In the autoclave the dispersion was subject for 20 minutes to a temperature of 121° C. and a pressure of 2 bar.

At the end of the process, the dispersion was subject to dialysis (Visking tubing, cut-off: 12000-14000) for 3 hours against distilled water so as to purify the nanohydrogels of the drug not encapsulated inside them.

After the dialysis, HA-CH nanohydrogels loaded with levofloxacin having dimensions of 150±20 nm were obtained, with a polydispersion index of 0.20±0.05.

To evaluate the effectiveness of entrapment of the drug in the HA-Rfv and HA-CH nanohydrogels, they were lyophilised and solubilised in N-methyl-pyrrolidone so as to break the nanohydrogels and release the levofloxacin trapped inside them. The entrapment effectiveness (encapsulation %) was determined by the ratio of the quantity of levofloxacin encapsulated in the nanohydrogels with respect to the total quantity of nanohydrogels produced, by means of spectrophotometer.

The entrapment effectiveness of the levofloxacin in the HA-Rfv nanohydrogels was 15% with respect to the weight of the polymer, while in the HA-CH NHs it was 5% with respect to the weight of the polymer.

Example 7

Purification Tests on the Ha-Rfv (Starting From Derivatized Polymer at 90% Mol/mol) By Means of Ultracentrifugation and Comparison with the HA-Cholesterol System For the preparation of HA-Rfv NHs starting from derivatized polymer at 90% mol/mol, 100 mg of hyaluronic acid in the form of tetrabutylammonium (HA) salt were dissolved in 10 mL of N-methylpyrrolidone (NMP) at ambient temperature; 120 mg of N-(6-bromohexyl)-tetrabutylriboflavin were dissolved in 1 mL of NMP and the solution was added to that of the polymer, leaving under stirring for 48 hours at ambient temperature. The reaction was then dialysed (cut-off 12000-14000) and lyophilised, obtaining 140 g of derivative as yellow lyophile (HA-Rfv). The degree of derivatization of the polymer was 90% mol/mol (moles of Rfv based on moles of repetitive units of HA, determined by spectrophotometer).

3 mg of the product were dispersed in 3 ml of water and left under stirring on a plate for 12 hours. The dispersion resulting from the water solution was placed in a closed glass container which was placed in an autoclave. In the autoclave the dispersion was subject for 20 minutes to a temperature of 121° C. and a pressure of 2 bar. At the end of the treatment, HA-Rfv nanohydrogels are obtained having dimensions of 350±15 nm, with a polydispersion index of 0.20±0.05.

The HA-CH NHs were prepared starting from derivatized polymer at 20% mol/mol, prepared as described in example 6 starting from HA and CH-Br; subsequently, 3 mg of the polymer HA-CH were dispersed in 3 ml of water and the resulting solution was left under stirring in a plate for 12 hours. The dispersion deriving from the water solution was placed inside a closed glass container which was placed in an ultrasonic bath and subject to ultrasounds for 25 min. At the end of the treatment, HA-CH nanohydrogels are obtained having dimensions of 120±20 nm, with a polydispersion index of 0.25±0.05.

The two NH dispersions (HA-Rfv and HA-CH) obtained as indicated above were subject to ultracentrifugation (40,000 rpm for 3 h at 4° C.). At the end of the process, both the supernatants were withdrawn, frozen in liquid nitrogen and lyophilised in order to determine the quantity of non-assembled polymer in NHs and therefore not precipitated. The lyophilised supernatants were weighed, obtaining 0.9 mg of product for the HA-Rfv and 2.1 mg of product for the HA-CH. It was ascertained that the HA-Rfv system has an NH formation yield of 70% w/w of the polymer used, while the HA-CH has an NH formation yield of 30% w/w.

Example 8

Preparation of HA-Rfv NHs (Starting from Derivatized Polymer at 30% Mol/mol) Chemically Bonded to the Enzyme HRP (Horseradish Peroxidase)

A suspension of HA-Rfv NHs (1 mg/mL, 5 mL) was prepared as described in example 1. 250 microL of water solution of EDC.HCl (1-(3-Dimethylaminopropyl)-3-ethylcarbodiimide hydrochloride) 2.9 mg/mL, 250 microL of water solution of NHS (N-hydroxysuccinimide) and 1.5 mL of HRP solution in a phosphate buffer (1 mg/mL) were added to the suspension and the reaction was left for 40 hours at 4° C. in the dark. At the end, the NHs-HRP product was purified by ultracentrifugation (40000 rpm, 3 hours, 4° C.; the pellet containing the NHs-HRP was re-suspended in 5 mL of water and kept at 4° C., while the supernatant was analysed by UV-Vis spectrophotometer or HPLC to quantify the quantity of protein not bound to the nanogels. The result of the analysis shows that the quantity of protein chemically bonded to the nanogels is 10% w/w with respect to the dry weight of the nanogels, or 20% w/w with respect to the initial quantity of protein used.

From the description of the above examples it is evident that the present invention has the great advantage of providing an extremely versatile and innovative platform for the preparation of polysaccharide-based nanohydrogels for applications in drug delivery.

The nanohydrogels subject of the present invention derive from an amphiphilic polysaccharide matrix synthesised from riboflavin or derivatives thereof. Said nanohydrogels can simultaneously encapsulate or adsorb a great number of active ingredients via different techniques.

It should be highlighted that the method subject of the present invention allows the preparation of nanohydrogel starting from different polysaccharides with different load and molecular weight, using riboflavin derivatives as hydrophobizing agents which, bonded to different degrees to the polymer chains, induce self-assembling of the system in a water environment. Furthermore, said process starting from the above-mentioned polymers can be performed by means of various procedures such as sonication, nanoprecipitation or autoclaving, according to the needs and application of the end product. The nanohydrogels thus obtained are stable in water and, unlike many nanohydrogels currently used, also in physiological conditions.

Furthermore, the nanogels thus formed can be subject to autoclaving in order to make them sterile.

Furthermore, the nanogels produced according to the above-mentioned method can be loaded with drugs via different techniques, such as polymer/drug co-precipitation, loading a preformed drug from a film, loading in autoclave, showing an entrapment capacity superior to that of the nanohydrogels currently produced.

Lastly, it should be underlined that the method of the present invention is not directed exclusively at biomedical and/or pharmaceutical applications, but can be effectively applied to all those applications that require the use of polysaccharide nanohydrogels, for example also in the field of cosmetics, cosmetic surgery and food.

The invention claimed is:

1. A method to prepare nanohydrogel comprising the steps of:
   functionalizing a polysaccharide with a hydrophobic compound to form a functionalized polysaccharide; and
   subjecting the functionalized polysaccharide to a self-assembling process in a water environment so as to form nanohydrogel;
   wherein said hydrophobic compound is riboflavin, or a derivative thereof, which is bound to an alkyl group having a functional group that is suited to form a covalent bond with the polysaccharide.

2. The method to prepare nanohydrogel according to claim 1, wherein the riboflavin derivative is an ester or urethane derivative obtained through reaction on hydroxyl groups of the riboflavin.

3. The method to prepare nanohydrogel according to claim 2, wherein the riboflavin derivative is tetrabutylriboflavin or tetraacetylriboflavin.

4. The method to prepare nanohydrogel according to claim 1, wherein said alkyl group is a straight chain containing 2 to 20 atoms, and in that said functional group is suited to react with the —OH or —NH groups available on the riboflavin, thus forming ester bonds, amide bonds, ether bonds or urethane bonds.

5. The method to prepare nanohydrogel according to claim 4, wherein said alkyl group is a straight chain containing 3 to 8 carbon atoms.

6. The method to prepare nanohydrogel according to claim 1, wherein the polysaccharide used can have the nature of a polyanion, of a polycation or a neutral nature as well as a molecular weight ranging from 2,000 to 1,500,000 and form, together with the riboflavin or the riboflavin derivative, ester bonds, amide bonds, ether bonds or alkyl bonds with a derivatization percentage ranging from 2 to 100% mol/mol.

7. The method to prepare nanohydrogel according to claim 6, wherein the polysaccharide is comprised in the group consisting of hyaluronic acid, pullulan, dextran, gellan, scleroglucan, chitosan, alginate, guar, xanthan, chitosan, cyclodextrins.

8. Nanohydrogel particles, which are manufactured with the method claimed in claim 1.

9. The nanohydrogel particles according to claim 8, wherein the nanohydrogel particles are chemically or physically loaded with a pharmacologically active compound.

* * * * *